June 18, 1946. T. J. MORRIS Plant Pat. 697
ROSE PLANT
Filed Oct. 10, 1945
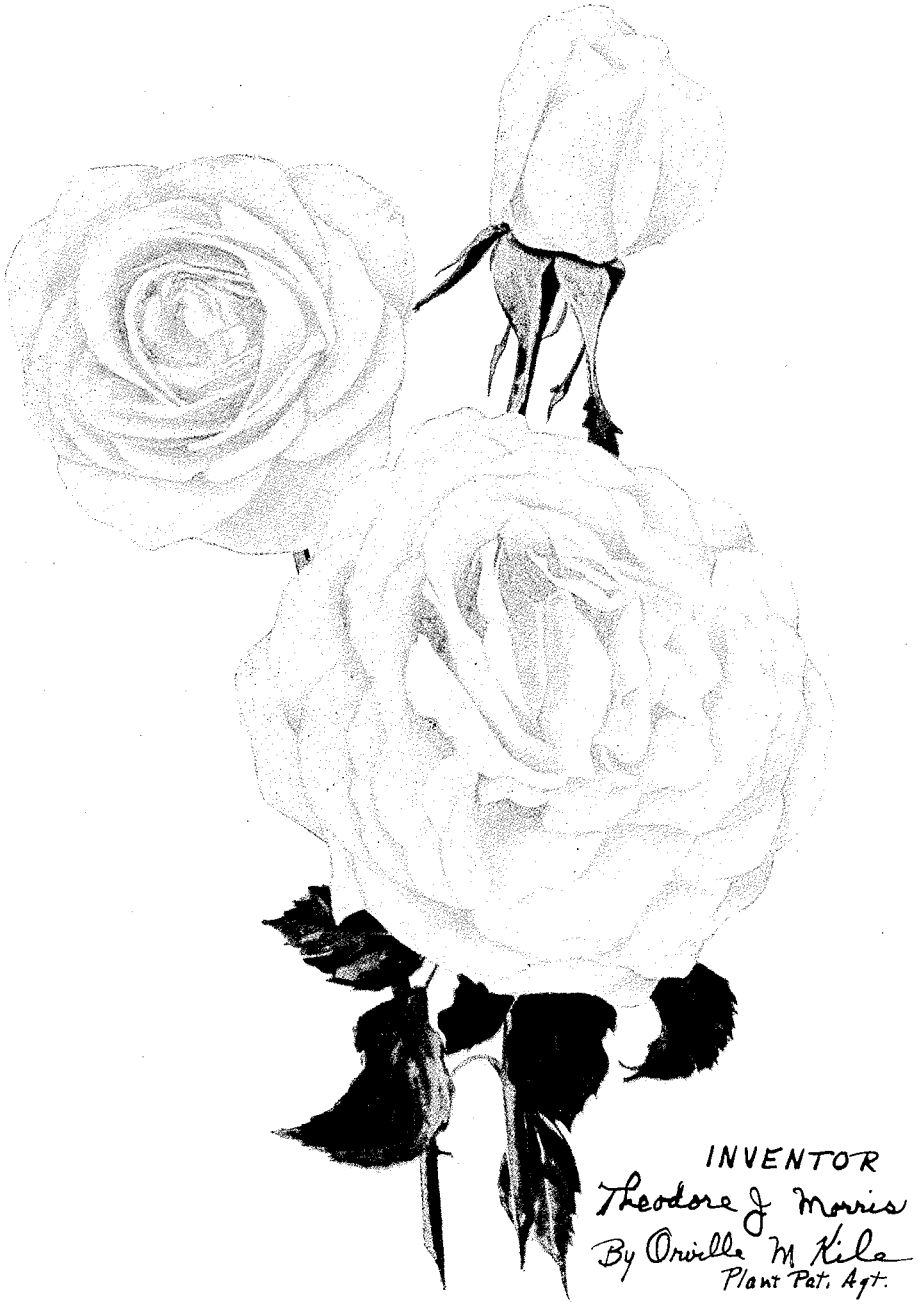

Patented June 18, 1946

Plant Pat. 697

UNITED STATES PATENT OFFICE

697

ROSE PLANT

Theodore J. Morris, Van Nuys, Calif., assignor to Germain Seed and Plant Company, Los Angeles, Calif.

Application October 10, 1945, Serial No. 621,476

1 Claim. (Cl. 47—61)

My present invention is a new and distinct variety of hydrid tea rose plant and relates particularly to improvements in pink flowing varieties.

This new variety originated as the result of definite breeding efforts carried on by me and resulted from a cross between Texas Centennial as the pollen parent and an unnamed seedling previously developed by me, as the seed parent. The combination of its color, fragrance and vigor is quite outstanding.

The accompanying illustration shows three specimens of the flowers of my new variety in various stages of opening, in as nearly the true colors as the artist could portray them.

Following is a detailed description of my new variety. Color plate designations refer to the British Horticultural Colour Chart except where otherwise indicated.

*The plant*

Growth: Upright and exceptionally vigorous.
Form: Bush.
Blooming habit: Very profuse and continuous bloomer.
Wood: New wood, reddish green; old wood, dark green.
*Bark.*—Smooth.
*Thorns.*—*Quantity*—ordinary. *Position*—irregular. *Color*—when young, green and red, brown when old. *Form*—narrow base, long, hooked downward. No prickles or needles on lateral stalks.
Bud:
*Size.*—Medium.
*Forms.*—Long and pointed.
*Color.*—Both sides of petals, Rose Madder (Plate 23/1).
*Opening.*—Buds open slowly; are not affected by adverse conditions.
*Calyx.*—Smooth, broad and cup-shaped. Has briar odor when rubbed.
*Peduncle.*—Long, stiff, wiry, smooth and medium green.
Bloom:
*Borne.*—Singly on long stems, but sometimes with as many as seven to a shoot on the bottom shoots.
*Size.*—Large, measuring 4½ to 4¾ inches in diameter.
*Form.*—High centered, retaining its form to the end.
*Color.*—Center of flower, Rose Bengal (Plate 25/2); inside petals, Rose Bengal (Plate 25/1); outside petals, Phlox Pink (Plate 625/1); reverse of petals, Rose Madder (Plate 23/2) to Tyrian Rose (Plate XII of Ridgway's Color Standards); aiglet, Canary Yellow (Plate 2/2); general tonality of color, Rose Madder (Plate 23/1).
*Discoloration.*—General tonality of color at end of first day, Rose Madder (Plate 23/1); second day, Phlox Pink (Plate 625); third day, Rose Madder (Plate 23/2).
*Petalage.*—Very double, averaging 48 petals in July in southern California. Few petaloids present.

Petals:
*Texture.*—Thick and heavy.
*Appearance.*—Satiny inside and outside. Veins prominent.
*Form.*—Round with notch at top.
*Arrangement.*—Regular.
*Fragrance.*—Intense; tea.
*Persistence.*—Drop off cleanly.
*Lasting quality.*—Exceedingly long lasting both on bush and as cut flower.
Genital organs:
*Stamens.* — *Anthers* — many, medium in length, yellow, arranged regularly around styles. *Filaments*—medium size, yellow. *Pollen*—golden yellow.
*Pistils.*—*Styles*—bunched, even, medium size. *Stigmas*—yellow.
*Ovaries.*—Some protrude from calyx.
*Fruit.*—(Variety is sterile with its own pollen.) *Form* — funnel-shaped. *Aspect* — smooth. *Sepals* — permanent, spear-shaped. *Color at maturity*—Russet.

*Comparison*

The variety most like my new variety is Catherine Kordes, the principal differences being as follows:

1. The flowers of the two varieties are in different color ranges, my variety being in the dark pink class while the Catherine Kordes is in the scarlet-carmine range.
2. My new variety has much more vigor of growth.
3. My new variety is a much more prolific bloomer.
4. The flowers of my new variety have more fragrance.
5. The flowers of my variety last longer as cut flowers.

Having thus disclosed my invention, I claim:

The new and useful variety of hybrid tea rose plant substantially as shown and described, characterized particularly by its great vigor of growth, its prolific blooming habit, and the intense fragrance, good keeping qualities and predominantly rose madder color of its flowers.

THEODORE J. MORRIS.